United States Patent
Shankar et al.

(10) Patent No.: US 9,738,766 B2
(45) Date of Patent: Aug. 22, 2017

(54) ORGANOPHOSPHORUS COMPOUNDS FOR FLAME RETARDANT POLYURETHANE FOAMS

(71) Applicant: Dow Global Technologies LLC, Midland, MI (US)

(72) Inventors: Ravi B. Shankar, Midland, MI (US); Matthew Martin Yonkey, Sanford, MI (US); YuDong Qi, Shanghai (CN); Nahrain E. Kamber, Penllyn, PA (US)

(73) Assignee: Dow Global Technologies LLC, Midland, MI (US)

( * ) Notice: Subject to any disclaimer, the term of this patent is extended or adjusted under 35 U.S.C. 154(b) by 152 days.

(21) Appl. No.: 14/433,728

(22) PCT Filed: Oct. 8, 2012

(86) PCT No.: PCT/CN2012/082580
§ 371 (c)(1),
(2) Date: Apr. 6, 2015

(87) PCT Pub. No.: WO2014/056138
PCT Pub. Date: Apr. 17, 2014

(65) Prior Publication Data
US 2015/0274915 A1    Oct. 1, 2015

(51) Int. Cl.
| | |
|---|---|
| *C08J 9/04* | (2006.01) |
| *C08J 9/00* | (2006.01) |
| *C09K 21/12* | (2006.01) |
| *C08K 5/5333* | (2006.01) |
| *C08K 5/5353* | (2006.01) |
| *C08K 5/5357* | (2006.01) |
| *C07F 9/6571* | (2006.01) |
| *C07F 9/40* | (2006.01) |
| *C07F 9/6574* | (2006.01) |
| *C08G 18/08* | (2006.01) |
| *C08G 18/48* | (2006.01) |
| *C08G 18/76* | (2006.01) |

(52) U.S. Cl.
CPC .......... *C08J 9/0038* (2013.01); *C07F 9/4006* (2013.01); *C07F 9/4075* (2013.01); *C07F 9/65742* (2013.01); *C07F 9/657181* (2013.01); *C08G 18/14* (2013.01); *C08G 18/4833* (2013.01); *C08G 18/7621* (2013.01); *C08K 5/5333* (2013.01); *C08K 5/5353* (2013.01); *C08K 5/5357* (2013.01); *C09K 21/12* (2013.01); *C08J 2375/08* (2013.01)

(58) Field of Classification Search
CPC C07F 9/4006; C07F 9/4075; C07F 9/657181; C07F 9/65742; C08G 18/14; C08G 18/4833; C08G 18/7621; C08J 9/0038; C08J 2375/08; C08K 5/5333; C08K 5/5353; C08K 5/5357; C08K 21/12
See application file for complete search history.

(56) References Cited

U.S. PATENT DOCUMENTS

| | | |
|---|---|---|
| 3,746,572 A | 7/1973 | Weil et al. |
| 3,969,437 A | 7/1976 | Shim |
| 4,022,852 A | 5/1977 | Vollmer |
| 4,172,863 A | 10/1979 | Waldmann |
| 4,857,364 A | 8/1989 | Von Bonin |
| 5,055,458 A | 10/1991 | Bailey et al. |
| 5,108,994 A | 4/1992 | Harnden et al. |
| 2010/0137465 A1* | 6/2010 | Stowell ............... C07F 9/65742 521/107 |
| 2011/0182973 A1 | 7/2011 | Schaefer-Korting et al. |

FOREIGN PATENT DOCUMENTS

| | | |
|---|---|---|
| CN | 101619076 | 1/2010 |
| WO | 2007014352 | 2/2007 |
| WO | 2008005555 | 1/2008 |

OTHER PUBLICATIONS

Cristau, et al., "Synthesis of Bis(hydroxymethyl) phosphorylated Compounds, analogs of a-aminophosphonic acids or alkylidenebisphosphonic acids"; Tetrahedron, vol. 57 (2001) (8 pgs).

\* cited by examiner

*Primary Examiner* — John Cooney
(74) *Attorney, Agent, or Firm* — Brooks, Cameron & Huebsch, PLLC

(57) ABSTRACT

An organophosphorus compound useful in a phosphorus containing flame retardant and a flame retardant polyurethane foam, where the organophosphorus compound is shown in Formula (I) where Y is selected from the group consisting of an —OH group, an —NH$_2$ group, an —NHR$^3$ group, and an —SH group, where R$^3$ is a monovalent hydrocarbyl group having 1 to 10 carbon atoms; R is a divalent hydrocarbyl group; X is a heteroatom group; and R$^1$ and R$^2$ are each independently a substituted or unsubstituted hydrocarbyl group, wherein R$^1$ and R$^2$ can be optionally joined to form a ring.

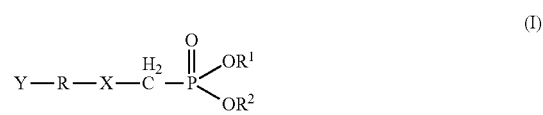

(I)

11 Claims, No Drawings

ORGANOPHOSPHORUS COMPOUNDS FOR FLAME RETARDANT POLYURETHANE FOAMS

This application is a National Stage Application under 35 U.S.C. §371 of International Application Number PCT/CN2012/082580, filed Oct. 8, 2012 and published as WO 2014/056138 on Apr. 17, 2014, the entire contents of which are incorporated herein by reference in its entirety.

FIELD OF THE DISCLOSURE

The disclosure relates generally to flame retardant materials, and more specifically to flame retardant polyurethanes and flame retardant polyurethane foams.

BACKGROUND

Halogen-containing flame retardants (FRs), such as trichloropropylphosphate (TCPP), may eventually be phased out or banned from use due to regulatory pressures and/or market demand for non-halogenated materials. As an FR, TCPP is used primarily in polyurethane (PU) foams. As such, there is a need to find a suitable non-halogenated FR for use in PU foams, especially flexible PU foams.

SUMMARY

The present disclosure provides an organophosphorus compound of Formula (I):

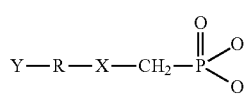

Formula I where Y is selected from the group consisting of an —OH group, an —$NH_2$ group, an —$NHR^3$ group, and an —SH group, where $R^3$ is a monovalent hydrocarbyl group having 1 to 10 carbon atoms; R is a divalent hydrocarbyl group; X is a heteroatom group; and $R^1$ and $R^2$ are each independently a substituted or unsubstituted hydrocarbyl group, wherein $R^1$ and $R^2$ can be optionally joined to form a ring, with the proviso that when Y is a hydroxyl group, X is an oxygen atom and R is —$CR^5_2$—$CR^5_2$—, where each $R^5$ is independently a hydrogen group or a hydrocarbyl group having 1 to 4 carbon atoms, then $R^1$ and $R^2$ join to form a ring.

The present disclosure also includes a phosphorus-containing flame retardant that includes an admixture of a polyol and the organophosphorus compound of Formula (I), where Y is selected from the group consisting of an —OH group, an —$NH_2$ group, an —$NHR^3$ group, and an —SH group, where $R^3$ is a monovalent hydrocarbyl group having 1 to 10 carbon atoms, R is a divalent hydrocarbyl, X is a heteroatom group, and $R^1$ and $R^2$ are each independently a substituted or unsubstituted hydrocarbyl group, wherein $R^1$ and $R^2$ can be optionally joined to form a ring.

The present disclosure also includes a flame retardant polyurethane foam that is a reaction product of an isocyanate, the phosphorus containing flame retardant discussed herein and a foaming agent.

For the various embodiments, the divalent hydrocarbyl group of R can have 1 to 20 carbon atoms. The heteroatom group X can be selected from the group consisting of an oxygen atom, a sulfur atom, an —$N(R^4)$— group, a selenium atom, a —$PR^4(O)$— group, a sulfoxide (—S(O)—) group, sulfone (—$S(O)_2$—) group, where $R^4$ is a substituted or unsubstituted hydrocarbyl group. For the organophosphorus compound of Formula (I) $R^1$ and $R^2$ can each be independently a hydrocarbyl group having 1 to 10 carbon atoms.

DETAILED DESCRIPTION

Embodiments of the present disclosure include an organophosphorus compound that is useful in forming flame retardant polyurethanes. The organophosphorus compound of the present disclosure can be incorporated into formulations used to form flame retardant polyurethanes, such as flame retardant polyurethane foams. The organophosphorus compound is reactive with the isocyanate compound used in forming the flame retardant polyurethanes and so is covalently bonded by way of the urethane groups, for example, in the flame retardant polyurethanes.

The flame retardant polyurethanes of the present disclosure can be produced by the reaction product of a polyol, or a mixture of polyols, having primary and/or secondary hydroxyl or amine groups; an isocyanate, a polyisocyanate, or a mixture thereof; and the organophosphorus compound of the present disclosure, where the organophosphorus compound has an isocyanate reactive group. The reaction used to produce the flame retardant polyurethanes of the present disclosure can also include a foaming agent to allow for the formation of flame retardant polyurethane foams. Other reactants and additives can include, but are not limited to, catalysts, crosslinkers, chain extenders, surfactants and/or stabilizers, among other additives, as discussed herein.

Embodiments of the organophosphorus compound used in forming flame retardant polyurethanes are shown in Formula (I):

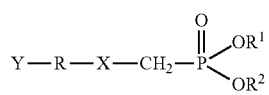

Formula I where Y is selected from the group consisting of an —OH group, an —$NH_2$ group, an —$NHR^3$ group, and an —SH group, where $R^3$ is a monovalent hydrocarbyl group having 1 to 10 carbon atoms; R is a divalent hydrocarbyl group; X is a heteroatom group; and $R^1$ and $R^2$ are each independently a substituted or unsubstituted hydrocarbyl group, wherein $R^1$ and $R^2$ can be optionally joined to form a ring, with the proviso that when Y is a hydroxyl group, X is an oxygen atom and R is —$CR^5_2$—$CR^5_2$—, where each $R^5$ is independently a hydrogen group or a hydrocarbyl group having 1 to 4 carbon atoms, then $R^1$ and $R^2$ join to form a ring.

The divalent hydrocarbyl group of R can have 1 to 20 carbon atoms. In one embodiment, the divalent hydrocarbyl group of R can have 2 to 4 carbon atoms. The heteroatom group X can be selected from the group consisting of an oxygen atom, a sulfur atom, an —$N(R^4)$— group, a selenium atom, a —$PR^4(O)$— group, a sulfoxide (—S(O)—) group, sulfone (—$S(O)_2$—) group, where $R^4$ is a substituted or unsubstituted hydrocarbyl group. For the organophosphorus compound of Formula (I) $R^1$ and $R^2$ can each independently be a hydrocarbyl group having 1 to 10 carbon atoms. In one embodiment, for the organophosphorus compound of Formula (I) $R^1$ and $R^2$ can each independently be a hydrocarbyl group having 1 to 4 carbon atoms.

As used herein, "substituted" (as applicable to $R^1$, $R^2$ and $R^4$) means containing an ether group or a dialkylamino group, such as, for example, the following structures (once the group is attached to the —P=O group):

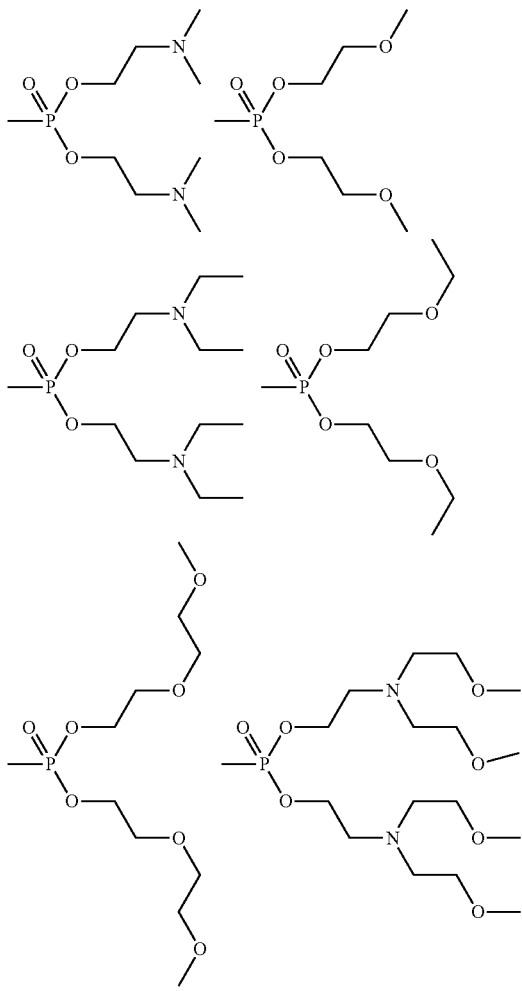

As used herein, a "divalent hydrocarbyl group" means a group formed by removing two hydrogen atoms from a hydrocarbon, the free valencies of which are not engaged in a double bond (e.g., 1,3-phenylene, —CH$_2$CH$_2$CH$_2$— propane-1,3-diyl, —CH$_2$— methylene).

As used herein, a "hydrocarbyl group" means univalent groups formed by removing a hydrogen atom from a hydrocarbon (e.g., methyl, ethyl, propyl).

As used herein, a "heteroatom group" is a group containing at least one heteroatom that is not a carbon atom or a hydrogen atom.

For the various embodiments, the organophosphorus compound of Formula I can have Y as a hydroxyl group, X as an oxygen atom, and $R^1$ and $R^2$ can be joined to form a ring of Formula (II):

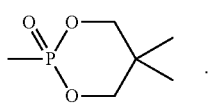

Formula II

For example, the organophosphorus compound of Formula I can have Y as a hydroxyl group, X as an oxygen atom, $R^1$ and $R^2$ can be jointed to form the ring of Formula (II), and R can be a divalent hydrocarbyl group —CR$^5_2$—CR$^5_2$— to provide the organophosphorus compound of Formula (III):

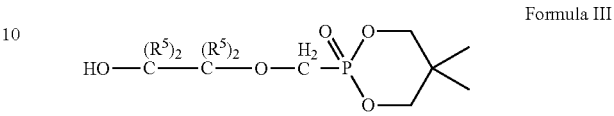

Formula III where each $R^5$ is independently a hydrogen group, or a hydrocarbyl group having 1 to 4 carbon atoms. At least two of the $R^5$ groups can, when each is a hydrocarbyl group having 1 to 4 carbon atoms, optionally join to form a ring.

In one embodiment, the organophosphorus compound of Formula I can have Y as a hydroxyl group, X as an oxygen atom, $R^1$ and $R^2$ can be joined to form the ring of Formula (II), and R can be a divalent hydrocarbyl group having 2 carbon atoms as provided in the organophosphorus compound of Formula (III), where each $R^5$ is a hydrogen group to provide the organophosphorus compound of Formula (IV):

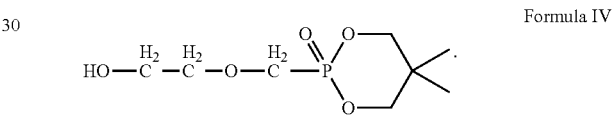

Formula IV

In another embodiment, the organophosphorus compound of Formula I can have Y as a hydroxyl group, X as an oxygen atom, $R^1$ and $R^2$ can be joined to form the ring of Formula (II), and where R is a divalent hydrocarbyl group having 3 carbon atoms to provide the organophosphorus compound of Formula (V):

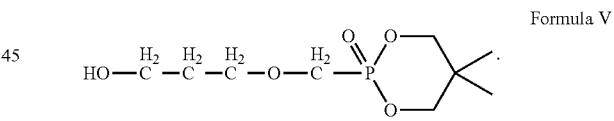

Formula V

It has also been discovered that the organophosphorus compound of Formula IV when present in a phosphorus containing flame retardant, as discussed hererin, can exist in a dynamic equilibrium state with an isomer the following Formula VI:

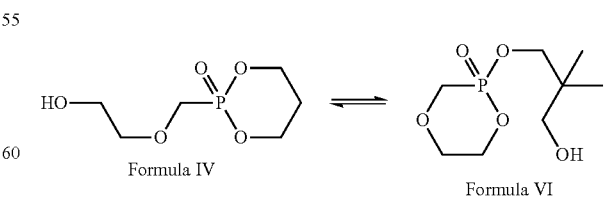

Formula IV        Formula VI

As seen in this equilibrium reaction, a new six-member ring forms in Formula VI with the phosphonate group of Formula W. The organophosphorus compound of Formula VI is useful in forming flame retardant polyurethanes of the present disclosure, as the hydroxyl group is present for reaction with an isocyanate group.

In an additional embodiment, the organophosphorus compound can have Y as a hydroxyl group; R as a divalent hydrocarbyl group having 2 carbon atoms; X as an oxygen atom and $R^1$ and $R^2$ each having two carbon atoms to provide the organophosphorus compound of Formula (VII):

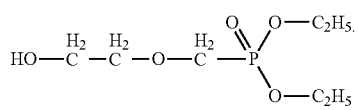

Formula VII

In one embodiment, the organophosphorus compound can have Y as a hydroxyl group; R as a divalent hydrocarbyl group having 3 carbon atoms; X as an oxygen atom and $R^1$ and $R^2$ each having two carbon atoms to provide the organophosphorus compound of Formula (VIII):

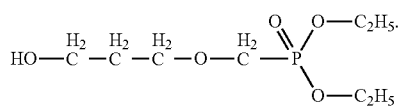

Formula VIII

As shown, the organophosphorus compounds of the present disclosure are halogen-free. As used herein, the term "halogen-free" means that the organophosphorus compound does not contain any one of the elements fluorine, chlorine, bromine and/or iodine.

The present disclosure also includes a phosphorus containing flame retardant. The phosphorus containing flame retardant is an admixture of a polyol and the organophosphorus compound of Formula (I):

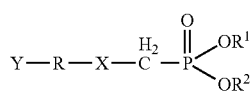

Formula I where Y is selected from the group consisting of an —OH group, an —NH$_2$ group, an —NHR$^3$ group, and an —SH group, where $R^3$ is a monovalent hydrocarbyl group having 1 to 10 carbon atoms, R is a divalent hydrocarbyl, X is a heteroatom group, and $R^1$ and $R^2$ are each independently a substituted or unsubstituted hydrocarbyl group, wherein $R^1$ and $R^2$ can be optionally joined to form a ring.

As discussed herein, R can be a divalent hydrocarbyl group having 1 to 20 carbon atoms. The heteroatom group X can be selected from the group consisting of an oxygen atom, a sulfur atom, an —N(R$^4$)— group, a selenium atom, a —PR$^4$(O)— group, a sulfoxide (—S(O)—) group, sulfone (—S(O)$_2$—) group, where $R^4$ is a substituted or unsubstituted hydrocarbyl group. $R^1$ and $R^2$ can each independently be a hydrocarbyl group having 1 to 10 carbon atoms.

The possible structures for the organophosphorus compound for use in the phosphorus containing flame retardant of the present disclosure include, but are not limited to, those illustrated and discuss for Formulae III through VIII, as discussed herein.

The present disclosure also includes a flame retardant polyurethane foam, discussed herein, that is a reaction product of an isocyanate, the phosphorus-containing flame retardant ,as discussed herein, and a foaming agent.

The organophosphorus compound can be in a liquid state at temperatures used in processing and/or forming the phosphorus containing flame retardant and/or the flame retardant polyurethane foam of the present disclosure. The processing temperatures are those temperatures suitable for introducing and reacting the components used in forming the phosphorus containing flame retardant and/or the flame retardant polyurethane (e.g., a flame retardant polyurethane foam). These temperatures can include 20° C. to 80° C.

Embodiments encompass mixing the organophosphorus compound and the polyol, both as discussed herein, to form an admixture of the phosphorus containing flame retardant of the present disclosure. In general components of the phosphorus containing flame retardant may be mixed together using, for example, mixing equipment described in the "Polyurethane Handbook", by G. Oertel, Hanser Gardner Publications.

The polyol includes those compounds having at least one group containing an active hydrogen atom capable of undergoing reaction with an isocyanate. Suitable polyols are known in the art and include those described herein and other commercially available polyols, as are known. Mixtures of two or more polyols and/or two or more polymer polyols may also be used to produce the phosphorus containing flame retardant according to embodiments of the present disclosure.

The organophosphorus compound may be present in the admixture of the phosphorus containing flame retardant at concentrations of 0.1 wt. % to 35 wt. % based on the total weight of the phosphorus containing flame retardant. All individual values and subranges from 0.1 wt. % to 35 wt. % are included herein and disclosed herein; for example, the organophosphorus compound may be from a lower limit of 0.1, 0.5, 1, 2, 3, 4, 5, 6, 7, 8, 9, 10, 11, 12, 13,14, 15, 16, 17, 18, 19, 20,21, 22, 23, 24, 25, 26, 27, 28, 29 or 30 wt % of total polyol blend, to an upper limit of 1, 2, 3, 4, 5, 6, 7, 8, 9, 10, 11,12, 13,14, 15, 16, 17, 18, 19, 20, 21, 22, 23, 24, 25, 26, 27, 28, 29, 30, or 35 wt % of the total phosphorus containing flame retardant.

For the present disclosure, polyols, or mixtures of two or more polyols, having primary and/or secondary hydroxyl or amine groups are suitable for producing the phosphorus containing flame retardant and the flame retardant polyurethane foams of the present disclosure. The polyols generally have at least two hydrogen atoms that are reactive towards isocyanates and can have a nominal functionality ranging from 2 to 10, a number average molecular weight of 100 to 10,000 (e.g., such as 200 to 7,000), and an average hydroxyl number ranging from 20 to 800 mg KOH/g.

Useful polyols include polyether polyols, polyester polyols, polyhydroxy-terminated acetal resins, polyetheresters, polycarbonates, polyesteramides, polyalkylene carbonate-based polyols, and hydroxyl-terminated amines and polyamines. Examples of these and other suitable isocyanate-reactive materials are described more fully in, for example, U.S. Pat. No. 4,394,491.

Embodiments encompass polyether polyols prepared by adding an alkylene oxide, such as ethylene oxide, propylene oxide, butylene oxide, or a combination thereof, to an initiator having from 2 to 8 active hydrogen atoms. Catalysis for this polymerization can be either anionic or cationic, with catalysts such as KOH, CsOH, boron trifluoride, or a double metal cyanide complex (DMC) catalyst such as zinc hexacyanocobaltate.

The initiators for the production of the polyols may have 2 to 8 functional groups that will react with alkylene oxides. Examples of suitable initiator molecules are water, organic dicarboxylic acids, such as succinic acid, adipic acid, phthalic acid and terephthalic acid and polyhydric, in particular dihydric to pentahydric alcohols or dialkylene glycols, for example ethanediol, 1,2- and 1,3-propanediol, diethylene glycol, dipropylene glycol, 1,4-butanediol, 1,6-hexanediol, glycerol, trimethylolpropane, pentaerythritol, sorbitol, and sucrose or blends thereof. Other initiators include compounds linear and cyclic compounds containing a tertiary amine such as ethanoldiamine, triethanoldiamine, and various isomers of toluene diamine.

Embodiments may encompass amine initiated polyols which are initiated with an alkyl amine as given by the formula below or containing an alkyl amine as part of the polyol chain.

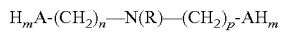

$$H_mA\text{-}(CH_2)_n\text{—}N(R)\text{—}(CH_2)_p\text{-}AH_m$$

where n and p are independently integers from 2 to 6, A at each occurrence is independently an oxygen or a nitrogen, m is equal to 1 when A is oxygen and is 2 when A is nitrogen.

In one embodiment, the polyol can include at least one of polyoxalkylene polyol having an equivalent weight of 900 to 2500. Such polyols may have a combined nominal functionality of 2 to 10. The polyoxalkylene may include polyoxyethylene, polyoxypropylene, or a combination of both. In some embodiments, the polyols may be initiated with glycerol, sucrose, sorbitol, novolac or a combination of at least two of them. In some embodiments, the polyols may be polyoxyethylene capped and have a polyoxyethylene percentage of 5 to 70 percent (%). Examples include VORANOL 3010, VORANOL CP1421, SPECFLEX NC630, SPECFLEX NC 632, VORALUX HF 505, VORALUX HF505HA, VORANOL 280, VORANOL CP260, VORANOL CP450, VORANOL CP 6001, VORANOL IP585, VORANOL RA800, VORANOL RA640, VORANOL RH360, VORANOL RN411, VORANOL RN482, and VORANOL RN490, all available from The Dow Chemical Company. Embodiments also include using a mixture of different embodiments of these polyols.

Embodiments encompass sorbitol initiated polyoxypropylene polyols with an equivalent weight of 100 to 200, such as VORANOL RN482 available from The Dow Chemical Company.

Embodiments encompass polyoxyethylene polyoxypropylene polyols initiated with a blend of glycerol and sucrose and having an equivalent weight of 1,000 to 2500 and a polyoxyethylene percentage of 15% to 40%, such as VORANOL 280 available from The Dow Chemical Company.

Representative polyester polyols include those obtained from polycarboxylic acids and polyhydric alcohols. Examples of suitable polycarboxylic acids include oxalic acid, malonic acid, succinic acid, glutaric acid, adipic acid, pimelic acid, suberic acid, azelaic acid, sebacic acid, maleic acid, fumaric acid, glutaconic acid, α-hydromuconic acid, β-hydromuconic acid, α-butyl-α-ethyl-glutaric acid, α,β-diethylsuccinic acid, isophthalic acid, terephthalic acid, hemimellitic acid, and 1,4-cyclohexane-dicarboxylic acid. Polyhydric alcohol (including both aliphatic and aromatic) may be used. Examples include ethylene glycol, 1,3-propylene glycol, 1,2-propylene glycol, 1,4-butylene glycol, 1,3-butylene glycol, 1,2-butylene glycol, 1,5-pentane diol, 1,4-pentane diol, 1,3-pentane diol, 1,6-hexane diol, 1,7-heptane diol, glycerol, 1,1,1,-trimethylolpropane, 1,1,1-trimethylolethane, hexane-1,2,6-triol, α-methyl glucoside, pentaerythritol, sorbitol, and sucrose or blends thereof. Also included are compounds derived from phenols such as 2,2-(4,4'-hydroxyphenyl)propane, commonly known as bisphenol A, bis(4,4'-hydroxyphenyl)sulfide, and bis-(4,4'-hydroxyphenyl)sulfone.

The polyols may, for example, be poly(propylene oxide) homopolymers, random copolymers of propylene oxide and ethylene oxide in which the poly(ethylene oxide) content is, for example, from 1 to 30% by weight, ethylene oxide-capped poly(propylene oxide) polymers and ethylene oxide-capped random copolymers of propylene oxide and ethylene oxide. For slabstock foam applications, such polyethers can contain 2-5, 2-4 or from 2-3, mainly secondary hydroxyl groups per molecule and have an equivalent weight per hydroxyl group of from 400 to 3000, especially from 800 to 1750. For high resilience slabstock and molded foam applications, such polyethers can contain 2-6 or 2-4, mainly primary hydroxyl groups per molecule and have an equivalent weight per hydroxyl group of from 1000 to 3000, especially from 1200 to 2000. When blends of polyols are used, the nominal average functionality (number of hydroxyl groups per molecule) can be in the ranges specified herein. For viscoelastic foams shorter chain polyols with hydroxyl numbers above 150 are also used. For the production of semi-rigid foams, trifunctional polyols with a hydroxyl number of 30 to 80 can be used.

The polyether polyols may contain low terminal unsaturation (for example, less that 0.02 meq/g or less than 0.01 meq/g), such as those made using DMC catalysts. Polyester polyols typically contain about 2 hydroxyl groups per molecule and have an equivalent weight per hydroxyl group of 400 to 1500.

The polyols may be polymer polyols. In a polymer polyol, polymer particles are dispersed in the conventional petroleum-based polyol. Such particles are widely known in the art and include styrene-acrylonitrile (SAN), acrylonitrile (ACN), polystyrene (PS), methacrylonitrile (MAN), polyurea (PHD), or methyl methacrylate (MMA) particles.

In addition to the above-described polyols, the polyol blend may also include other ingredients such as catalysts, silicone surfactants, preservatives, and/or antioxidants.

The phosphorus-containing flame retardant can be used in the production of polyurethane products, such as polyurethane foams, elastomers, microcellular foams, adhesives, coatings, etc. For example, the phosphorus-containing flame retardant may be used in a formulation for the production of a fire resistant polyurethane and/or a fire resistant polyurethane foam. In general, the fire resistant polyurethane foam can be prepared as a reaction product of an isocyanate, the phosphorus containing flame retardant, as discussed herein, and a foaming agent. It is possible to also use, optionally, a catalyst(s) and/or other optional ingredients as desired under conditions such that the isocyanate and the phosphorus containing flame retardant react to form a polyurethane and/or polyurea polymer while the foaming agent generates a gas that expands the reacting mixture.

Process techniques for producing polyurethane products are known in the art. In general components of the polyurethane forming reaction mixture may be mixed together in a convenient manner, for example, by using any of the mixing equipment described in the prior art for the purpose such as described in "Polyurethane Handbook", by G. Oertel, Hanser Gardner Publications. For example, the present disclosure provides a process for production of the flame retardant polyurethane foams by the reaction of the isocyanate(s), and/or polyisocyanate(s), the phosphorus-containing flame retardant, as discussed herein, and a foaming agent. The organophosphorus compound of the phosphorus containing flame retardant of the present disclosure has only one isocyanate reactive group.

The relative amounts of the reactants in forming the flame retardant polyurethane foam are based on 100 parts by weight of the polyol used in the reaction. So, for the various embodiments the amount of isocyanate and/or polyisocyanate used in forming the flame retardant polyurethane foam can be from 50 to 600 parts per 100 parts by weight of the polyol.

In an additional embodiment, the amount of isocyanate and/or polyisocyanate used in forming the flame retardant polyurethane foam can be from 80 to 400 parts per 100 parts by weight of the polyol. The amount of the organophosphorus compound in the phosphorus containing flame retardant can be from greater than 0 parts to 50 parts per 100 parts by weight of the polyol. As used herein, greater than 0 parts means that an amount (e.g., an amount of the organophosphorus compound) is present in the reaction mixture used to form the flame retardant polyurethane foam.

In an additional embodiment, the amount of the organophosphorus compound in the phosphorus containing flame retardant can be from 0.1 parts to 40 parts per 100 parts by weight of the polyol, or from 1 parts to 30 parts per 100 parts by weight of the polyol. The amount of the foaming agent used in forming the flame retardant polyurethane foam can be from 1 to 50 parts per 100 parts by weight of the polyol.

Other optional components used in forming the flame retardant polyurethane foam of the present disclosure can include 0.1 parts to 10 parts of a catalyst, per 100 parts by weight of the polyol, as discussed herein. Another optional component used in forming the flame retardant polyurethane foam of the present disclosure can include up to 20 parts of a crosslinking agent, as discussed herein, per 100 parts by weight of the polyol used in forming the flame retardant polyurethane foam of the present disclosure. It is also possible to optionally use up to 10 parts of a surfactant, as discussed herein, per 100 parts by weight of the polyol used in forming the flame retardant polyurethane foam of the present disclosure.

As used herein the flame retardant polyurethane foams of the present disclosure can include flexible foams, having a low degree of crosslinking and low resistance to deformation under pressure, and rigid foams, which have a higher degree of crosslinking and a higher resistance to deformation under pressure. The production of either a flexible polyurethane foam or a rigid polyurethane foam can be influenced by the structure and molar mass of the polyol and the reactivity and number (functionality) of the hydroxy groups present in the polyol. The polyurethane foams can therefore be produced in the form of rigid or flexible foams by selection of the starting materials as is known.

Foams can be formed according to a number of different processes. These processes include, but are not limited to, a cold-curing process, a slab foaming process or via the twin-conveyor-belt process, as are known. The process permits production of flame retardant polyurethane foams in the form of rigid or flexible foams in continuous or batch production mode or in the form of foamed shaped products.

The foam may be formed by the so-called prepolymer method, in which a stoichiometric excess of the isocyanate is first reacted with the high equivalent weight polyol(s) in the phosphorus containing flame retardant to form a prepolymer, which is in a second step reacted with a chain extender and/or water to form the desired foam. Frothing methods are also suitable. So-called one-shot methods may also be used. In such one-shot methods, the isocyanate and all isocyanate-reactive materials are simultaneously brought together and caused to react. Three widely used one-shot methods which are suitable for use in this disclosure include slabstock foam processes, high resilience slabstock foam processes, and molded foam methods.

Slabstock foam is conveniently prepared by mixing the foam ingredients and dispensing them into a trough or other region where the reaction mixture reacts, rises freely against the atmosphere (sometimes under a film or other flexible covering) and cures. In common commercial scale slabstock foam production, the foam ingredients (or various mixtures thereof) are pumped independently to a mixing head where they are mixed and dispensed onto a conveyor that is lined with paper or plastic. Foaming and curing occurs on the conveyor to form a foam bun.

In the production of rigid polyurethane foams, the foaming agent includes water, and mixtures of water with a hydrocarbon. The amount of water is may be in the range of 2 to 15 parts by weight, or from 2 to 10 parts by weight based on 100 parts by weight of the polyol. The amount of hydrocarbon to be combined with the water is suitably selected depending on the desired density of the foam, and may be less than about 40 parts by weight, or less than about 30 parts by weight based on 100 parts by weight of the polyol. When water is present as an additional foaming agent, it is may be present in an amount between about 0.5 and 10 parts by total weight of the total polyol composition.

Molded foam can be made according to the disclosure by transferring the reactants (the isocyanate, phosphorus containing flame retardant, foaming agent, and optional surfactant) to a closed mold where the foaming reaction takes place to produce a shaped foam. Either a so-called "cold-molding" process, in which the mold is not preheated significantly above ambient temperatures, or a "hot-molding" process, in which the mold is heated to drive the cure, can be used. Cold-molding processes are suitable to produce high resilience molded foam.

As discussed herein, the flame retardant polyurethane or fire resistant polyurethane foam can be formed with an isocyanate, a polyisocyanate, or a mixture thereof. Examples of suitable isocyanates and/or polyisocyanates include aliphatic, cycloaliphatic, arylaliphatic and/or aromatic isocyanates.

Aliphatic, cycloaliphatic, arylaliphatic, aromatic and aromatic isocyanates can have the general formula $Q(NCO)_n$, in which n can be from 2 to 4 or from 2 to 3, and Q can be an aliphatic hydrocarbon radical having from 2 to 18 or from 6 to 10, carbon atoms, a cycloaliphatic hydrocarbon radical having from 4 to 15 or from 5 to 10, carbon atoms, an aromatic hydrocarbon radical having from 6 to 15, or from 6 to 13, carbon atoms, or an araliphatic hydrocarbon radical having from 8 to 15, or 8 to 13, carbon atoms.

Examples of suitable aromatic isocyanates include the 4,4'-, 2,4' and 2,2'-isomers of diphenylmethane diisocyante (MDI), blends thereof and polymeric and monomeric MDI blends, toluene-2,4- and 2,6-diisocyanates (TDI), m- and p-phenylenediisocyanate, chlorophenylene-2,4-diisocyanate, diphenylene-4,4'-diisocyanate, 4,4'-diisocyanate-3,3'-dimethyldiphenyl, 3-methyldiphenyl-methane-4,4'-diisocyanate and diphenyletherdiisocyanate and 2,4,6-triisocyanatotoluene and 2,4,4'-triisocyanatodiphenylether. An example of a toluene diisocyanate includes, but is not limited to, VORANATE T-80 from The Dow Chemical Company.

Mixtures of isocyanates may be used, such as the commercially available mixtures of 2,4- and 2,6-isomers of toluene diisocyantes. A crude polyisocyanate may also be used in the practice of this disclosure, such as crude toluene diisocyanate obtained by the phosgenation of a mixture of toluene diamine or the crude diphenylmethane diisocyanate obtained by the phosgenation of crude methylene diphenylamine. TDI/MDI blends may also be used.

Examples of aliphatic polyisocyanates include ethylene diisocyanate, 1,6-hexamethylene diisocyanate, isophorone diisocyanate, cyclohexane 1,4-diisocyanate, 4,4'-dicyclohexylmethane diisocyanate, 1,3-bis(isocyanatomethyl)cyclohexane, 1,4-bis(isocyanatomethyl)cyclohexane, saturated analogues of the mentioned aromatic isocyanates, and mixtures thereof.

For the production of flexible foams, the polyisocyanates may often be the toluene-2,4- and 2,6-diisocyanates or MDI or combinations of TDI/MDI or prepolymers made therefrom.

Examples of foaming agents include those substances known for production of polyurethane foams. Examples include water, gases (e.g., carbon dioxide), volatile organic compounds (e.g., n-pentane, isopentane, cyclopentane) and halogen-containing alkanes (e.g., trichloromethane, methylene chloride, chlorofluoroalkanes). A mixture of a plurality of foaming agents can also be used.

The amount of foaming agent used in forming the flame retardant polyurethane foams can also depend upon the foaming agent used. For example, when water is used as the foaming agent, useful amounts of the water can include molar amounts greater than 0 up to 1 mole of water per mole of the isocyanate groups available for reaction with the water (the molar amount of the isocyanate groups available for reaction with the water is the difference between the molar amount of all of the isocyanate groups used and the molar amount, with the exception of the water, of the hydrogen atoms reactive towards isocyanate groups).

The reaction mixture used to form the fire resistant polyurethane foam of the present disclosure may also include additional ingredients such as catalysts, crosslinkers, emulsifiers, silicone surfactants, preservatives, other flame retardants, colorants, antioxidants, reinforcing agents, fillers, including recycled polyurethane foam in form of powder, as discussed hererin.

Examples of other flame retardants which can optionally be present in the flame retardant polyurethane foams of the present disclosure, in addition to the organophosphorus compound, include compounds, such as triethyl phosphate, triphenyl phosphate, diphenyl cresyl phosphate, tricresyl phosphate, isopropylated or butylated aryl phosphates, aromatic bisphosphates, neopentyl glycol bis(diphenyl phosphate), chlorine-containing phosphoric esters, e.g. tris(chloroisopropyl) phosphate or tris(dichloropropyl) phosphate, dimethyl methanephosphonate, diethyl ethanephosphonate, dimethyl propanephosphonate, oligomeric phosphates or phosphonates, phosphorus compounds containing hydroxy groups, 5,5-dimethyl-1,3,2-dioxaphosphorinane 2-oxide derivatives; phosphorus compounds of salt type, such as ammonium phosphate, ammonium polyphosphate, melamine phosphate, melamine polyphosphate, metal salts of dialkylphosphinic acids, metal salts of alkanephosphonic acids; nitrogen compounds, such as melamine, melamine cyanurate; chlorine compounds and bromine compounds, examples being alkyl esters of a tetrabromobenzoic acid, bromine-containing diols prepared from tetrabromophthalic anhydride, bromine- and/or chlorine-containing polyols, bromine-containing diphenyl ethers; and/or inorganic flame retardants, such as aluminum hydroxide, boehmite, magnesium hydroxide, zinc borate, expandable graphite and/or clay minerals.

Examples of catalysts that can be used in forming the flame retardant polyurethane foams of the present disclosure include, but are not limited to, tertiary amine compounds, amines with isocyanate reactive groups and organometallic compounds. Exemplary tertiary amine compounds include triethylenediamine, N-methylmorpholine, N,N-dimethylcyclohexylamine, pentamethyldiethylenetriamine, tetramethylethylenediamine, bis (dimethylaminoethyl)ether, 1-methyl-4-dimethylaminoethyl-piperazine, 3-methoxy-N-dimethylpropylamine, N-ethylmorpholine, dimethylethanolamine, N-cocomorpholine, N,N-dimethyl-N',N'-dimethyl isopropylpropylenediamine, N,N-diethyl-3-diethylamino-propylamine and dimethylbenzylamine. Exemplary organometallic catalysts include organomercury, organolead, organoferric and organotin catalysts, with organotin catalysts being preferred among these. Suitable tin catalysts include stannous chloride, tin salts of carboxylic acids such as dibutyltin di-laurate. A catalyst for the trimerization of isocyanates, resulting in an isocyanurate, such as an alkali metal alkoxide may also optionally be employed herein.

One or more crosslinkers may also be provided in the reactants that form the flame retardant polyurethane foams of the present disclosure, in addition to the polyols described herein. This is particularly the case when making high resilience slabstock or molded foam. The crosslinkers may have three or more isocyanate-reactive groups per molecule and an equivalent weight per isocyanate-reactive group of less than 400. The crosslinkers may include from 3-8 or from 3-4 hydroxyl, primary amine or secondary amine groups per molecule and have an equivalent weight of from 30 to 200, especially from 50 to 125. Examples of suitable crosslinkers include diethanol amine, monoethanol amine, triethanol amine, mono- di- or tri(isopropanol) amine, glycerine, trimethylol propane, pentaerythritol, and sorbitol.

It is also possible to use one or more chain extenders in forming the flame retardant polyurethane foams of the present disclosure. The chain extender may have two isocyanate-reactive groups per molecule and an equivalent weight per isocyanate-reactive group of up to 400, especially from 31 to 125. The isocyanate reactive groups can include hydroxyl, primary aliphatic or aromatic amine or secondary aliphatic or aromatic amine groups. Examples of chain extenders include amines ethylene glycol, diethylene glycol, 1,2-propylene glycol, dipropylene glycol, tripropylene glycol, ethylene diamine, phenylene diamine, bis(3-chloro-4-aminophenyl)methane and 2,4-diamino-3,5-diethyl toluene. If used, chain extenders are typically present in an amount from 1 to 50 or from 3 to 25 parts by weight per 100 parts by weight of polyol.

When used as described herein, the products made using the embodiments of the phosphorus containing flame retardant may exhibit better flame retardant properties than products made using comparative flame retardants such as trichloropropylphosphate, while at the same time maintaining good values for various physical properties such as tensile strength, tensile elongation, and tear strength. For example, the products described herein afford better FR performance at a lower concentration compared to products made using the halogen-containing trichloropropylphosphate.

For example, the embodied products may pass flame tests as developed by the State Of California, Department of Consumer Affairs, Bureau of Home Furnishings and Thermal Insulation, Technical Bulletin 117 (Requirements, Test Procedure and Apparatus for Testing the Flame Retardance of Resilient Filling Materials Used in Upholstered Furniture) of March 2000, section A part 1 (Cal 117).

Examples of the use of the products available according to the invention are as follows: furniture padding, textile inserts, mattresses, seats (e.g., aircraft seats and/or automobile seats), armrests and modules, and also seat coverings and cladding over technical equipment.

EXAMPLES

The following examples are provided to illustrate the embodiments of the disclosure, but are not intended to limit the scope thereof. All parts and percentages are by weight unless otherwise indicated.

Materials Used:

VORANOL 3010 (a polyol)—An about 994 equivalent weight polyoxyethylene polyoxypropylene capped polyoxypropylene polyol initiated with glycerol, having nominal functionality of 3, a polyoxyethylene percentage of around 8%, and an OH value of 56 mg KOH/g. Available from The Dow Chemical Company.

VORANOL CP1421 (a polyol)—An about 1,675 equivalent weight polyoxyethylene/polyoxypropylene capped polyoxypropylene polyol initiated with glycerol, having nominal functionality of 3, a polyoxyethylene percentage around 78%, and a hydroxyl number of about 32 mg KOH/g. Available from The Dow Chemical Company.

VORALUX HF505HA (a polyol) An about 1902 equivalent weight polyoxyethylene capped polyoxypropylene polyol initiated with sorbitol, having nominal functionality of 6, a polyoxyethylene percentage around 16%, and a hydroxyl number of about 29.5 mg KOH/g. Available from The Dow Chemical Company.

VORANATE T-80, toluene diisocyanate (an isocyanate) from The Dow Chemical Company.

Trichloropropylphosphate (TCPP), flame retardant from Zhangjiagang Changyu Chemical Co.,Ltd.

Deionized Water ($H_2O$) from The Dow Chemical Company.

N,N-Diethanolamine (DEOA), (for foaming action) OH value 1602, from Changzhou Jushun Chemical Company.

TEGOSTAB B-8681 (a silicone surfactant), commercially available from Evonik Industries.

DABCO 33-LV, NIAX A1 (3:1), (an amine catalyst) a 33% solution of triethylenediamine in propylene glycol available from Air Products & Chemicals Inc.

DABCO T-9 (a stannous octoate catalyst) available from Air Products & Chemicals Inc.

Niax L620, a silicon surfactant for polyether flexible slabstock foam, from Momentive.

Acetyl chloride, Sigma-Aldrich, 98%. Diethyl ether, Fisher Scientific, anhydrous. 1,3-dioxolane, Sigma-Aldrich, 99.8%. 1,3-dioxane, TCI America, >98%. Neopentylglycol, Sigma-Aldrich, 99%. 4-(Dimethylamino)pyridine, Sigma-Aldrich, >99%. Triethylamine, Sigma-Aldrich, ≥99%. Zinc chloride, Sigma-Aldrich, 1.0 M in diethyl ether. Triethyl phosphite, Sigma-Aldrich, 98%. Ethanol, Pharmco-AAPER, 200 proof anhydrous. Concentrated HCl, EMD Chemical, 36.5-38%. Methylene chloride, Fisher Scientific, Optima grade. O-Xylene, Sigma-Aldrich, ≥98%. Acetonitrile, Fisher Scientific, HPLC grade.

Organophosphorus Compound Example (OPC EX) 1

The reaction to produce OPC EX 1 is:

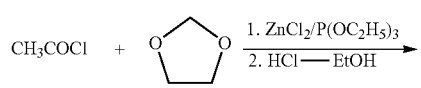

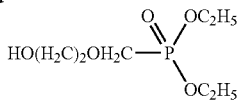

Prepare OPC EX 1 as follows. Add acetyl chloride (44 grams (g), 0.56 moles (mol)) in 50 milliliter (mL) of ether over 30 minutes (min) to an ice-cooled solution of 1,3-dioxolane (40 g, 0.54 mol) and zinc chloride /ether (2.1 mL, 1.0 millimoles (mmol)) in 150 mL of ether with stirring. Maintain the temperature of the reaction is between 15-22° C. with an ice water bath. Allow the resulting mixture to stir for 1 hour (hr) and concentrate under reduced pressure with bath temperature below 30° C. Treat the residue with triethyl phosphite (117 g, 0.70 mol) and gently warm to 85° C. After the reaction exotherm passes warm the reaction mixture to 120° C. for 30 min. Cool the reaction mixture to 45° C. Apply a vacuum and slowly warm the mixture to 80° C. to remove the excess triethyl phosphite and side products. Subject the residue, 134 g, to Kugelrohr distillation. Distill the desired material, 2-((diethoxyphosphoryl)methoxy)ethyl acetate, at 170° C. and 1.2 to 1.8 torr. The overall yield of the product is 103.75 g (75.6%).

Dissolve 2-((diethoxyphosphoryl)methoxy)ethyl acetate (54.3 g, 213 mmol) in 150 mL of ethanol containing concentrated HCl and reflux the mixture for 4 hr. Monitor the progress of the reaction by $^{31}P$ NMR. After 4 hrs of reflux the $^{31}P$ NMR shows cleanly 2 peaks in the ratio of 83:17 at 21.93 and 20.83 ppm with the lower amount corresponding to the starting material. Continuing the heating for 3 hrs leads to a ratio of 87:12. Con HCl (0.1 mL) is added and heated for 3 hrs. Concentrate the reaction mixture and then dilute with methylene chloride. Wash with sodium chloride solution, dry over anhydrous $MgSO_4$, filter and concentrate to yield clear oil, 42.3 g. (93%). The product is characterized by $^1H$, $^{31}P$ NMR and GC-MS.

OPC EX 2

The reaction to produce OPC EX 2 is:

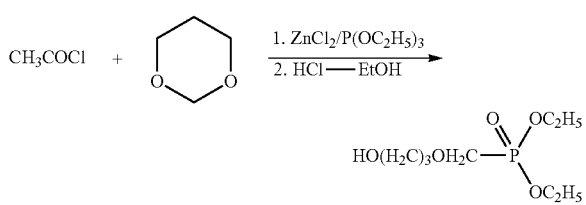

Prepare OPC EX 2 as follows. Add acetyl chloride (36.28 g, 0.46 mol) in 20 mL of diethylether over 20 min to an ice-cooled solution of 1,3-dioxane (34.11 g, 0.39 mol) and zinc chloride/ether (2.9 mL, 1.5 mmol) in 200 mL of ether with stirring. Maintain the temperature of the reaction between 15-22° C. with an ice water bath during addition. Allow the resulting mixture to slowly warm to room temperature over 2 hr and concentrate under reduced pressure with bath temperature below 35° C. Dilute the residue with o-xylene (40 mL) and add to hot (140° C.) triethyl phosphite (78.9 g, 0.47 mol) over a period of 45 minutes. Maintain temperature of 140° C. for 2 additional hr. Cool the reaction mixture to 45° C. Apply a vacuum and slowly warm the mixture to 80° C. to remove the excess triethyl phosphite and side products. Subject the residue to Kugelrohr distillation. Distill the desired material, 3-((diethoxyphosphoryl) methoxy) propyl acetate, at 170° C. and 0.5 torr.

Dissolve 3-((diethoxyphosphoryl)methoxy)propyl acetate (171.22 g, 0.638 mol) in 500 mL of ethanol containing concentrated HCl (2.0 mL) and reflux the mixture for 14 hr. Monitor the progress of the reaction by $^{31}$P NMR. Concentrate the reaction mixture and then dilute with chloroform. Wash with sodium chloride solution, dry over anhydrous MgSO$_4$, filter and concentrate to yield clear oil. Heat the residue to 160° C. under vacuum (1.2 torr) to remove volatile impurities. Product is obtained as clear colorless oil. The product is characterized by $^1$H, $^{31}$P NMR and GC-MS.

OPC EX 3

The reaction to produce OPC EX 3 is:

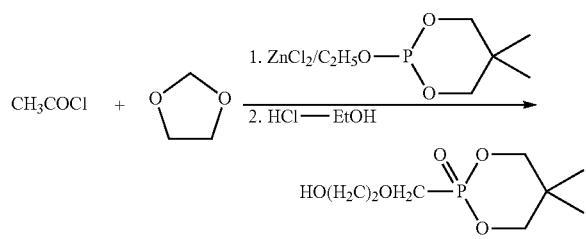

Prepare OPC EX 3 as follows. Add acetyl chloride (15.0 g, 0.20 mol) in 30 mL of ether over 30 min to an ice-cooled solution of 1,3-dioxolane (40 g, 0.54 mol) and zinc chloride /ether (2.0 mL, 1.0 mmol) in 50 mL of ether with stirring. Maintain the temperature of the reaction between 20-27° C. with an ice water bath. Allow the resulting mixture to stir for 2 hr and concentrated under reduced pressure with bath temperature below 30° C. Treat the residue with 2-ethoxy-5,5-dimethyl-1,3,2-dioxaphosphinane (39.68 g, 0.22 mol) and gently warm to 85° C. After the reaction exotherm passes warm the reaction mixture to 140° C. for 30 min. Cool the reaction mixture to 45° C. Apply a vacuum and slowly warm the mixture to 150° C. to remove the excess dimethyl-1,3,2-dioxaphosphinane and side products. The desired material is separated by chromatography on silica gel with ethyl acetate as eluant. The overall yield of the product is 32.0 g (59.4%).

Dissolve 2-((2-oxido-1,3,2-dioxaphosphinan-2-yl) methoxy)ethyl acetate (54.3 g, 213 mmol) in 150 mL of ethanol containing con (38%) HCl and reflux the mixture for 7 hr. Monitor the progress of the reaction by $^{31}$P NMR. Concentrate the reaction mixture and then dilute with methylene chloride. Wash with sodium chloride solution, dry over anhydrous MgSO$_4$, filter and concentrate to yield clear oil, 21.4 g. (89%). The $^1$H, $^{31}$P NMR and GC-MS show the product to be a mixture of 2 isomers (78:22) the major component being the depicted product.

OPC EX 4

The reaction to produce OPC EX 4 is:

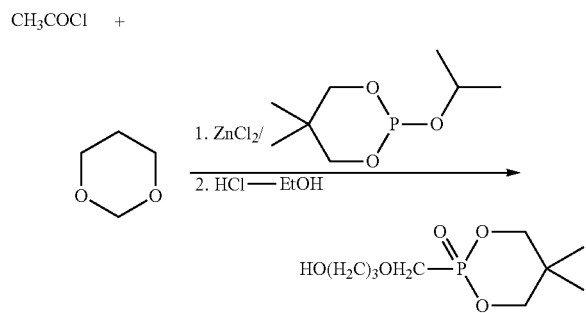

Prepare OPC EX 4 as follows. Add acetyl chloride (37.42 g, 0.48 mol) in 20 mL of diethylether over 20 min to an ice-cooled solution of 1,3-dioxane (34.11 g, 0.39 mol) and zinc chloride /ether (3.0 mL, 1.54 mmol) in 200 mL of ether with stirring. Maintain the temperature of the reaction between 15-22° C. with an ice water bath during addition. Allow the resulting mixture to slowly warm to room temperature over 2 hr and concentrate under reduced pressure with bath temperature below 35° C. Dilute the residue with o-xylene (50 mL) and add to hot (135° C.) 2-isopropoxy-5,5-dimethyl-1,3,2-dioxaphosphinane (86.14 g, 0.45 mol) over a period of 45 minutes. Maintain temperature of 140° C. for 2 additional hr. Allow reaction mixture to cool to room temperature and stir for 16 hr. Subject the residue to Kugelrohr distillation (160° C.@1.3 torr) to remove volatile impurities.

Dissolve 3-((5,5-dimethyl-2-oxido-1,3,2-dioxaphosphinan-2-yl)methoxy)propyl acetate (5.0 g, 18 mmol) in 30 mL of ethanol containing concentrated HCl (0.5 mL) and reflux the mixture for 4 hr. Monitor the progress of the reaction by $^{31}$P NMR. Concentrate the reaction mixture and then dilute with chloroform. Wash with sodium chloride solution, dry over anhydrous MgSO$_4$, filter and concentrate to yield clear oil, 3.4 g (78%). The product is characterized by $^1$H, and $^{31}$P NMR.

Fire Resistant Polyurethane Foam

Fire Resistant Polyurethane Foam Examples (FR PU Foam Ex) 6-9 and Comparative Example A Prepare FR PU Foam Ex 6-9 and Comparative Example A as follows. Prepare each of FR PU Foam Ex 6-9 and Comparative Example A through hand-mixed trials in a plastic cup. According to the amounts shown in Table 1, blend OPC EX 1 through OPC EX 4 (for FR PU Foam Ex 6-9) and TCPP (for Comparative Example A) with VORANOL 3010 at 3000 rotations-per-minute (rpm) using a high speed mixer (DC-CH4ORM from HSIANG TAI MACHINERY INDUSTRY CO., LTD). To each of the mixtures add the DABCO 33LV and MAX Al in a 3:1 ratio, the H$_2$O, the Niax L620 and the DABCO T-9, according to the amount shown in Table 1, and mix at 3000 rpm for one minute. Add VORANATE T-80 to each of the mixtures, according the amount shown in Table 1, under high speed blending (about 3000-4000 rpm) for about 6 seconds. The obtained composition was poured into an open box for foaming.

Test the foams according to the State Of California, Department of Consumer Affairs, Bureau of Home Furnishings and Thermal Insulation, Technical Bulletin 117 (Requirements, Test Procedure and Apparatus for Testing the Flame Retardance of Resilient Filling Materials Used in Upholstered Furniture) of March 2000, section A part 1 (Cal 117). Cut the flexible foams into specimens (304.8 mm×76.2 mm×12.7 mm) using an electric saw. For each formulation, test 10 specimens (5 before aging, 5 after aging). Expose each specimen to a flame for 12 seconds and then record After Flame Time (AFT) and Char Length.

Conduct resilience testing according to ASTM D3574-95-H by a Ball Rebound tester. Measure indentation load deflection (ILD) property using an Instron 5565 according to ASTM D3574-95-B1. Set the downward speed of the compressive plate to 50 millimeters/minute. Test the compressive strength at 40% (Indentation load deflection (ILD, KN/m$^2$) 40%).

As shown in Table 1 for Cal117 FR testing, the addition of the OPC EX 1-4 into a polyurethane foam system increases the fire resistance (FR) performance dramatically. The FR PU Foam Ex 6-9 having 7 parts of OPC EX 1-5 have better FR performance than Comparative Example A with 30 parts TCPP. Comparative Examples A failed the Cal 117 FR testing. The results show that OPC EX 1-4 afford better FR performance at lower loading compared to the halogen-containing TCPP. In addition, FR PU Foam Ex 6-9 have comparative mechanical properties with of the foam of Comparative Example A having TCPP.

blending (about 3000-4000 rpm) for about 6 seconds. The obtained composition was poured into an open box for foaming.

Test the foams according to Cal 117, as described for FR PU Foam Ex 6-9. Cut the flexible foams into specimens (304.8 mm×76.2 mm×12.7 mm) using an electric saw. For

TABLE 1

Formulations and Properties for FR PU Foam Ex 6-9 and Comparative Example A
(Amounts give in parts per 100 parts by weight polyol)

|  |  | Comparative Example A | FR PU Foam Ex 6 | FR PU Foam Ex 7 | FR PU Foam Ex 8 | FR PU Foam Ex 9 |
|---|---|---|---|---|---|---|
| Voranol 3010 | | 100 | 100 | 100 | 100 | 100 |
| DABCO 33-LV, NIAX A1 (3:1) | | 0.24 | 0.24 | 0.24 | 0.24 | 0.24 |
| $H_2O$ | | 4 | 4 | 4 | 4 | 4 |
| Niax L620 | | 1.2 | 1.2 | 1.2 | 1.2 | 1.2 |
| DABCO T-9 | | 0.22 | 0.22 | 0.22 | 0.22 | 0.22 |
| TDI Index | | 95 | 95 | 95 | 95 | 95 |
| TCPP | | 30 | | | | |
| OPC EX 1 | | | 7 | | | |
| OPC EX 2 | | | | 7 | | |
| OPC EX 3 | | | | | 7 | |
| OPC EX 4 | | | | | | 7 |
| VORANATE T-80 | | 51.1 | 52.6 | 52.6 | 52.6 | 52.6 |
| Mechanical property | | | | | | |
| Density (kg/m³) | | 30.9 | 28.5 | 28.9 | 26.3 | 24.7 |
| Resilience (%) | | 28 | 27 | 32 | 18.0 | 17.0 |
| ILD 40%, $KN/m^2$ | | 160.2 | 168 | 160 | 156.1 | 139.9 |
| FR performance Cal 117 testing | AFT before aging (sec) | 0 0 0 0 | 0 0 1 0 | 0 0 0 0 | 0 0 0 0 | 3 0 0 0 |
| | AFT after aging (sec) | □10 □10 0 0 | 0 1 0 0 | 2 3 0 0 | 0 0 0 0 | 6 1 0 0 |
| | Char length before aging (mm) | 30 25 35 30 | 60 65 50 60 | 50 45 50 55 | 55 50 50 55 | 80 80 75 80 |
| | Char length after aging (mm) | burn out burn out | 65 60 55 50 | 80 65 70 80 | 60 55 65 60 | 75 50 50 30 |
| | Pass or Fail | Fail | pass | pass | pass | pass |

FR PU Foam Ex 10-14 and Comparative Example B

Prepare FR PU Foam Ex 10-14 and Comparative Example B as follows. Prepare each of FR PU Foam Ex 10-14 and Comparative Example B through hand-mixed trials in a plastic cup. According to the amounts shown in Table 2, blend OPC EX 1 through OPC EX 4 (for FR PU Foam Ex 10-14) and TCPP (for Comparative Example B) with VORALUX HF505HA and VORANOL CP1421 at 3000 rotations-per-minute (rpm) using a high speed mixer (DC-CH40RM from HSIANG TAI MACHINERY INDUSTRY CO., LTD). To each of the mixtures add the DEOA, TEGOSTAB B8681, DABCO 33-LV and NIAX A1 in a 3:1 ratio, the $H_2O$, and the DABCO T-9, according to the amount shown in Table 2, and mix at 3000 rpm for one minute. Add VORANATE T-80 to each of the mixtures, according to the amount shown in Table 2, under high speed each formulation, test 10 specimens (5 before aging, 5 after aging). Expose each specimen to a flame for 12 seconds and then record After Flame Time (AFT) and Char Length.

Conduct resilience testing according to ASTM D3574-95-H by a Ball Rebound tester. Measure indentation load deflection property using an Instron 5565 according to ASTM D3574-95-B1. Set the downward speed of the compressive plate to 50 millimeters/minute. Test the compressive strength at 40% (ILD 40%).

As shown in Table 2 for Cal 117 FR testing, the addition of the OPC EX 1-4 into a polyurethane foam system increases the fire resistance (FR) performance dramatically. The FR PU Foam Ex 10-14 having 5 parts of OPC EX 1-4 have better FR performance than Comparative Example B with 15 parts TCPP. Comparative Examples B failed the Cal 117 FR testing. The results show that OPC EX 1-4 afford better FR performance at lower loading compared to the halogen-containing TCPP.

TABLE 2

Formulations and properties for FR PU Foam Ex 10-14 and Comparative Example B

| | | Comparative Example B | FR PU Foam Ex 11 | FR PU Foam Ex 12 | FR PU Foam Ex 13 | FR PU Foam Ex 14 |
|---|---|---|---|---|---|---|
| VORALUX HF505HA | | 100 | 100 | 100 | 100 | 100 |
| VORANOL CP1421 | | 2.5 | 2.5 | 2.5 | 2.5 | 2.5 |
| DEOA | | 1.67 | 1.67 | 1.67 | 1.67 | 1.67 |
| TEGOSTAB B8681 | | 1.2 | 1.2 | 1.2 | 1.2 | 1.2 |
| DABCO 33-LV, NIAX A1 (3:1) | | 0.2 | 0.2 | 0.2 | 0.22 | 0.22 |
| $H_2O$ | | 3.8 | 3.5 | 3.5 | 3.5 | 3.5 |
| DABCO T-9 | | 0.07 | 0.07 | 0.07 | 0.07 | 0.07 |
| TDI Index | | 108 | 108 | 108 | 108 | 108 |
| TCPP | | 15 | | | | |
| OPC EX 1 | | | 5 | | | |
| OPC EX 2 | | | | 5 | | |
| OPC EX 3 | | | | | 5 | |
| OPC EX 4 | | | | | | 5 |
| VORANATE T-80 | | 49.40 | 48.30 | 48.21 | 48.10 | 48.37 |
| Density (kg/m³) | | 30.6 | 33.3 | 29.3 | 33.1 | 35.4 |
| FR performance Cal 117 testing | AFT before aging (sec) | 9 | 1 | 0 | 0 | 0 |
| | | 14 | 0 | 0 | 0 | 0 |
| | | 0 | 1 | 0 | 0 | 0 |
| | | 0 | 0 | 0 | 0 | 0 |
| | AFT after aging (s) | >20 | 0 | 0 | 0 | 0 |
| | | >20 | 0 | 0 | 0 | 0 |
| | | 0 | 1 | 0 | 0 | 0 |
| | | 4 | 1 | 0 | 0 | 0 |
| | Char length before aging (mm) | 170 | 65 | 30 | 35 | 30 |
| | | 195 | 75 | 40 | 45 | 30 |
| | | 54 | 70 | 35 | 40 | 50 |
| | | 78 | 60 | 45 | 45 | 50 |
| | Char length after aging (mm) | burn out | 65 | 45 | 35 | 45 |
| | | burn out | 70 | 50 | 40 | 40 |
| | | 72 | 70 | 45 | 50 | 50 |
| | | 90 | 75 | 40 | 40 | 45 |
| | Pass or fail | fail | pass | pass | pass | pass |

The invention claimed is:

1. An organophosphorus compound of Formula (I):

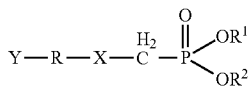

Formula I where Y is an —OH group;

R is —$CH_2$—$CH_2$—$CH_2$— or —$CR^5{}_2$—$CR^5{}_2$—, where each $R^5$ is independently a hydrogen group or a hydrocarbyl group having 1 to 4 carbon atoms;

X is an oxygen atom; and $R^1$ and $R^2$ join to form a ring of Formula (II):

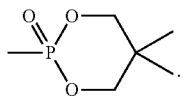

Formula II

2. The organophosphorus compound of claim 1, where the R is a divalent hydrocarbyl group having 2 carbon atoms to provide the organophosphorus compound of Formula (III):

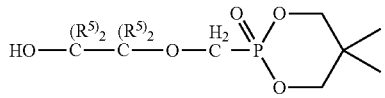

Formula III where each $R^5$ is independently a hydrogen group, or a hydrocarbyl group having 1 to 4 carbon atoms.

3. The organophosphorus compound of claim 2, where each $R^5$ is a hydrogen group to provide the organophosphorus compound of Formula (IV):

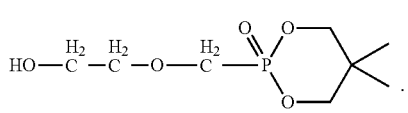

Formula IV

4. The organophosphorus compound of claim 1, where the R is a divalent hydrocarbyl group having 3 carbon atoms to provide the organophosphorus compound of Formula (V):

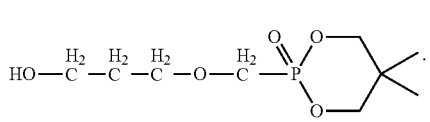

Formula V

5. A phosphorus containing flame retardant, comprising:
an admixture of:
   a polyol; and
   an organophosphorus compound of Formula (I):

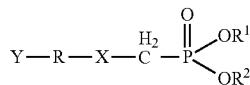

Formula I where Y is an —OH group;
R is —CH$_2$—CH$_2$—CH$_2$— or —CR$^5_2$—CR$^5_2$—, where each R$^5$ is independently a hydrogen group or a hydrocarbyl group having 1 to 4 carbon atoms;
X is an oxygen atom; and
R$^1$ and R$^2$ join to form a ring of Formula (II):

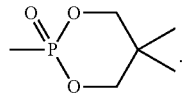

Formula II

6. The phosphorus containing flame retardant of claim 5, where the organophosphorus compound of Formula (I) has the structure of the organophosphorus compounds in claim 2.

7. The phosphorus containing flame retardant of claim 5, where R is a divalent hydrocarbyl group having 2 carbon atoms to provide the organophosphorus compound of Formula (IV):

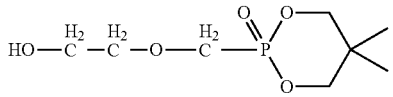

Formula IV where the organophosphorus compound of formula (IV) is in a dynamic equilibrium state with an isomer the following Formula VI:

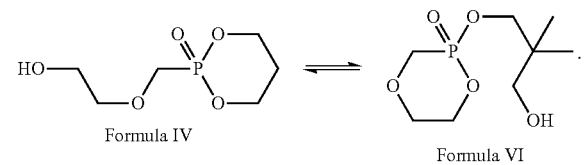

Formula IV          Formula VI

8. The phosphorus containing flame retardant of claim 5, where the polyol is a polyoxalkylene polyol having an equivalent weight of 900 to 2500 and a combined nominal functionality of 2 to 10.

9. A flame retardant polyurethane foam comprising,
a reaction product of:
   an isocyanate;
   a phosphorus containing flame retardant of claim 5; and
   a foaming agent.

10. The flame retardant polyurethane foam of claim 9, where flame retardant polyurethane foam includes 5 to 7 parts of the phosphorus containing flame retardant per 100 parts by weight of the polyol.

11. The phosphorus containing flame retardant of claim 5, where the organophosphorus compound of Formula (I) has the structure of the organophosphorus compounds in claim 4.

* * * * *